United States Patent [19]

McAleer et al.

[11] 4,018,222
[45] Apr. 19, 1977

[54] SYRINGE CONTAINING FROZEN VACCINE

[75] Inventors: William J. McAleer, Ambler; Maurice R. Hilleman, Lafayette Hill, both of Pa.

[73] Assignee: Merck & Co., Inc., Rahway, N.J.

[22] Filed: May 13, 1975

[21] Appl. No.: 577,244

Related U.S. Application Data

[63] Continuation-in-part of Ser. No. 548,467, Feb. 10, 1975.

[52] U.S. Cl. .............................. 128/216; 128/272; 206/365; 206/367
[51] Int. Cl.² .......................................... A61M 5/00
[58] Field of Search ......... 128/216, 215, 217, 218, 128/272, 214, 221, DIG. 24; 206/364–370, 438–441; 229/3.5 MF

[56] References Cited

UNITED STATES PATENTS

| | | | |
|---|---|---|---|
| 2,726,656 | 12/1955 | Lockhart | 128/216 |
| 2,895,475 | 7/1959 | Cole | 128/272 |
| 3,286,832 | 11/1966 | Pilger | 206/365 |
| 3,472,369 | 10/1969 | Schuster | 206/438 X |
| 3,576,650 | 4/1971 | Underwood et al. | 206/438 X |
| 3,685,720 | 8/1972 | Brady | 206/438 X |
| 3,761,013 | 9/1973 | Schuster | 206/439 X |

*Primary Examiner*—John D. Yasko
*Attorney, Agent, or Firm*—Donald J. Perrella; J. Jerome Behan

[57] ABSTRACT

Vaccine delivery system wherein an aqueous vaccine diluted to human dosage concentration is loaded into presterilized single dosage syringes having a squeezable body portion and wherein a plurality of these syringes are sealed inside a bag and the contents of the syringes are frozen to preserve the titer of the vaccine.

11 Claims, 7 Drawing Figures

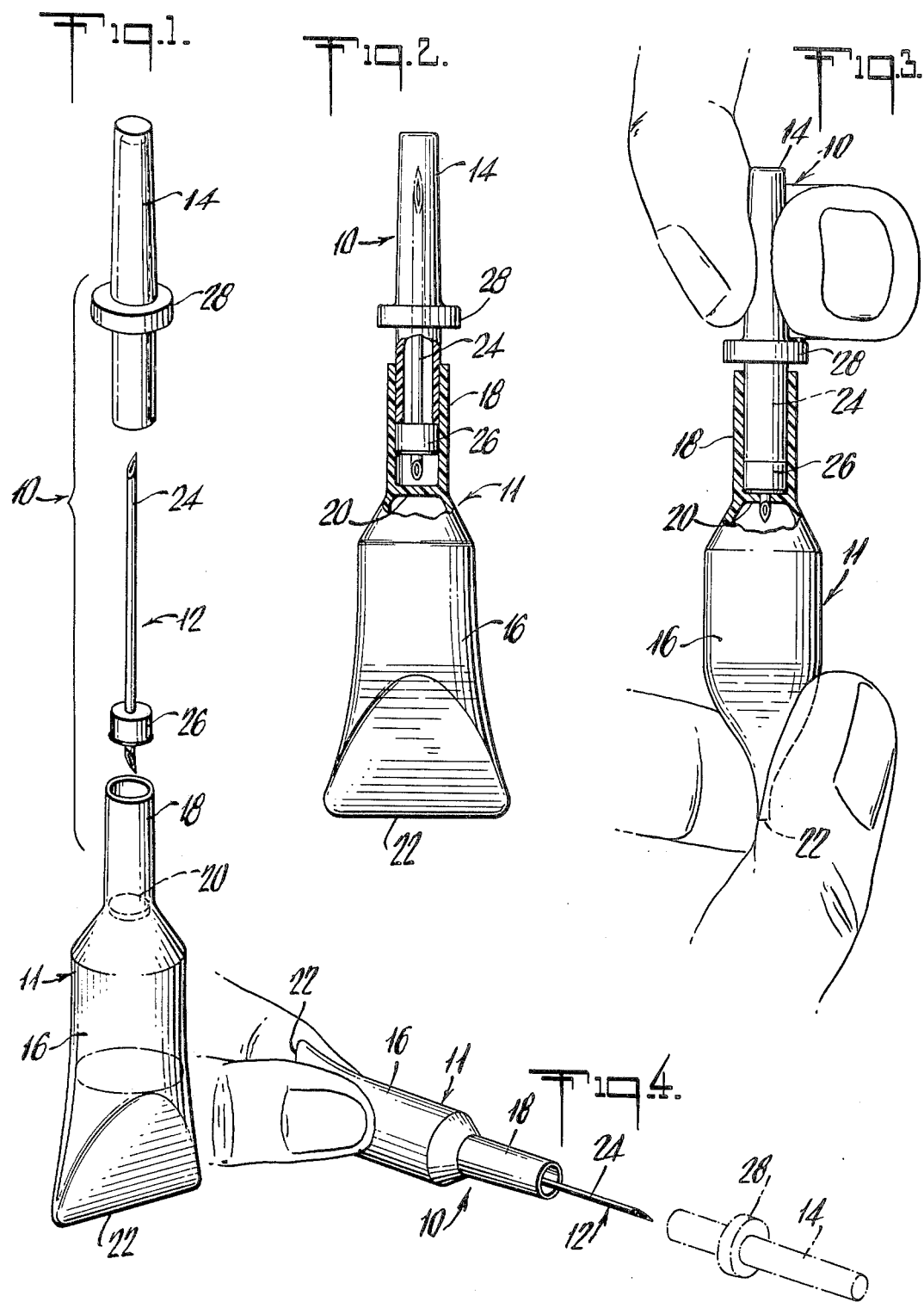

SYRINGE CONTAINING FROZEN VACCINE

RELATED APPLICATION

This application is a continuation-in-part of our copending application Ser. No. 548,467, filed Feb. 10, 1975.

BACKGROUND OF THE INVENTION

1. Field of the Invention

This invention relates to the delivery of vaccines and more particularly it concerns novel methods and apparatus for packaging and dispensing vaccines of the type which are administered by injection through a needle.

2. Description of the Prior Art

In general, vaccines, after being harvested from a culture tank, are clarified, diluted, subdivided into vials or ampules and then lyophilized. When lyophilized the vaccine may be kept for extended periods of time at low temperature, i.e., 4° C. with losses substantially below those encountered in aqueous vaccines. The lyophilized vaccine is supplied with diluent and occasionally with disposable syringes. In this latter case, the syringe itself may carry the diluent liquid which is injected into the vaccine ampule or vial just prior to administration. The diluent dissolves or suspends the vaccine and the vaccine is withdrawn back into the syringe for administration by injection.

The above described technique for vaccine delivery suffers from a number of drawbacks. Firstly, the lyophilization process results in a high loss of titer which in turn requires a high overcharge of vaccine. Further, storage results in an additional loss of titer which must be compensated for. In addition, there is a relatively high cost for the lyophilization operation itself. The cost of the conventional syringes is quite high. There is also the potential for incomplete suspension of the vaccine during rehydration and the possibility for contamination and additionally the technique is costly of the valuable time of the medical personnel doing the injections.

SUMMARY OF THE INVENTION

The present invention overcomes the above described difficulties and drawbacks of the prior art. Thus, the present invention provides a vaccine delivery system which does not require a plurality of components such as separate syringes and mixing vials. Moreover, the arrangement of the present invention permits the processing and delivery of aqueous vaccine to individual dosages with a minimum of titer loss so that a proper dosage is assured for each injection at a minimum cost. In addition, with the present invention, the vaccine and syringe are conveniently and fully sterilized in a manner which ensures that sterilization is preserved. The ease of operation combined with the economy of this unit makes it possible to bring this essential medical care to areas otherwise unprotected.

According to one aspect of the invention, there is provided a novel single dosage vaccine delivery system including a hypodermic syringe which comprises a container portion, a needle portion and a dust guard for the needle portion. The container portion is made of a plastic material which is flexible and resilient at room temperature. The container portion is filled with a single dose of aqueous vaccine diluted to a concentration suitable for human administration. The diluted aqueous vaccine, however, is frozen inside the syringe since the entire assembly is held at a temperature from about −10° C to about −20° C or lower. The needle portion of the syringe is conventional and consists of a hollow sharp needle for injection. The dust guard protects the needle portion of the syringe and helps to insure sterility. It may be made out of any type of the more rigid plastics such as polethylene, polypropylene, polyesters or the like.

While the composite system described above is held at a temperature of from about −10° C to about −20° C or lower, the active component does not lose its titer and the unit can be held for long periods of time in this state. To prepare the unit for use, one removes it from the low temperature storage chamber and allows it to come to room temperature. During this operation the vaccine returns to the fluid state, the plastic container recovers its flexibility and the unit is ready to be used for injection.

According to a further aspect of the invention, there is provided a novel package arrangement wherein a plurality of frozen vaccine containing syringes, as above described, are maintained together in a gas and light impervious bag or pouch (such as a metal foil bag) which protects the vaccine in the syringes from the deteriorating effects of light and carbon dioxide gas. The protection from the carbon dioxide gas is of particular importance when dry ice is used to maintain the low temperature of the entire assembly during shipment. The carbon dioxide, if it permeates the container portion of the syringe, may adversely affect the pH of the vaccine and its titer.

According to a still further aspect of the invention, there is provided a novel method of preparing vaccine for storage, delivery and administration. This method involves filling sterilized syringes with an aqueous vaccine diluted to human dosage concentration, sealing the syringes and then sealing a plurality of the syringes inside a gas and light impervious bag or pouch. The bag or pouch (such as a metal foil bag) is then subjected to a very low temperature to freeze the aqueous vaccine to retain its titer. The bags may then be placed in dry ice to keep the vaccine frozen. At the same time the bag protects the vaccine from the potentially deleterious effect of carbon dioxide gas which emanates from the dry ice. It is obvious, therefore, that the present invention provides an individual delivery system which would cost only a fraction of the delivery system now in use.

The present invention can also be applied to other biologicals such as influenza vaccines, bacterial vaccines, blood products and the like by establishing the specific conditions for optimal retention of potency for each case.

There has thus been outlined rather broadly the more important features of the invention in order that the detailed description thereof that follows may be better understood, and in order that the present contribution to the art may be better appreciated. There are, of course, additional features of the invention that will be described more fully hereinafter. Those skilled in the art will appreciate that the concepts on which this disclosure is based may readily be utilized as the basis for the designing of other methods and structures for carrying out the purposes of this invention. It is important therefore, that this disclosure be regarded as including such equivalent constructions and methods as do not depart from the spirit and scope of the invention.

BRIEF DESCRIPTION OF THE DRAWINGS

Several embodiments of the invention have been chosen for purposes of illustration and description, and are shown in the accompanying drawings, forming a part of the specification, wherein:

FIG. 1 is an explosed perspective view of a syringe portion of a vaccine delivery system according to the present invention;

FIG. 2 is a front elevational view, partially cut away, of the syringe of FIG. 1 in assembled condition;

FIG. 3 is a side elevational view of the syringe of FIG. 2 during a readying operation;

FIG. 4 is an exploded perspective view showing the syringe of FIG. 3 in condition for an injection operation;

DETAILED DESCRIPTION OF THE PREFERRED EMBODIMENTS

Figure 5:
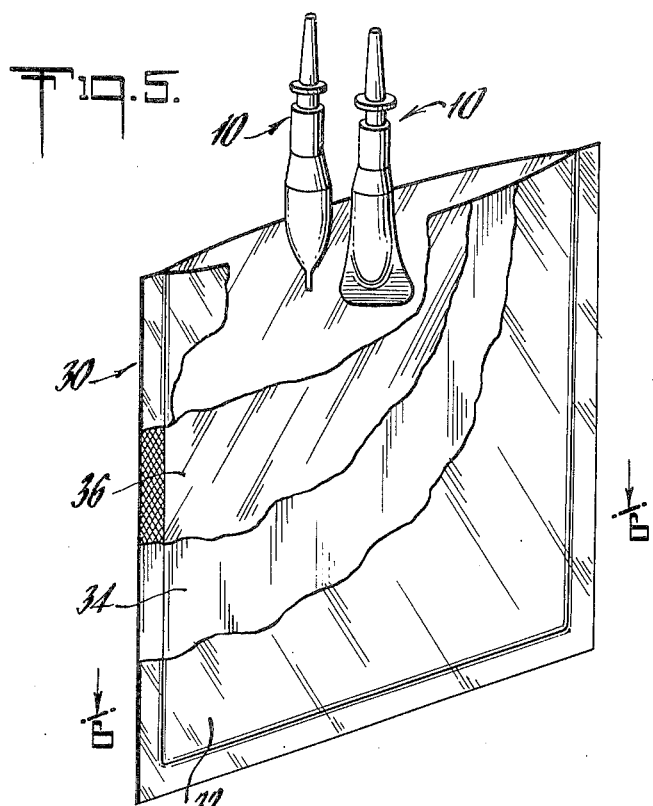
FIG. 5 is a perspective view, partially cut away, showing a container for holding syringes according to the present invention.

FIGS. 1-4 show a syringe 10, which is generally similar to those shown and described in U.S Pat. Nos. 1,687,502, 2,642,064, and 2,693,183.

As can be seen in FIG. 1, the syringe 10 comprises a container portion 11, a needle portion 12 and a dust guard 14. The container portion 11 is made of a soft plastic material which is resiliently flexible at room temperature. This material must be capable of remaining stable at very low temperatures, i.e., from about minus 10° C to about −20° C or below, and of recovering its resilient flexibility when returned to room temperature. Also, the material of the container portion 10 should be permeable to a gas sterilizing atmosphere such as ethylene oxide. Low density polyethylene has been found to be quite suitable for this purpose, although other plastics are equally useful.

The container portion 11 has a generally tubular main body region 16 which tapers inwardly at its upper end to a hollow cylindrical neck 18. A diaphragm 20 extends across the lower end of the neck 18 to close off the main body region 16. The lower end of the main body region is flattened and heat sealed closed as indicated at 22.

The needle portion 12 comprises a hollow elongated needle 24 which extends through, and is press fitted in, a metal collar 26. The needle 24 is cut on a bias at both ends to form penetrating points; in the one case, for injection into a patient, and in the other case, for piercing the diaphragm 20. The collar 26 is dimensioned to fit snugly but slideably in the cylindrical neck 18 as illustrated in FIG. 2.

The dust guard 14 is molded of a plastic material, such as polyethylene, nylon or polypropylene, which may be somewhat harder than the material of the container portion 10. The dust guard 14 is also of generally tubular configuration and is closed at its upper end and open at its lower end. A flange 28 is formed about the mid-portion of the dust guard. The region below the flange 28 as shown in FIG. 2, also fits snugly but slideably inside the neck 18 of the container portion 10. As can be seen, the dust guard 14 is of sufficient length to accommodate the needle 24 when the lower end of the dust guard presses against the collar 26. It will also be noted that the flange 28 is at a greater distance above the upper end of the neck 18 than the distance between the lower end of the needle 24 and the diaphragm 20.

The syringe assembly as shown in FIG. 2, maintains vaccine sealed in the main body region 16 of the container portion 10. To ready the syringe for an injection, the dust guard 14 is pushed down into the neck 18 to force the collar 26 and needle 24 downwardly until the lower end of the needle pierces the diaphragm 20 and opens into the main body region 16. The dust guard 14 is then removed, as shown in FIG. 4, and the syringe is ready for the administration of a dose of vaccine. The vaccine is administered by injecting the outer end of the needle 24 into a patient and then squeezing the main body region 16 to force the vaccine out through the needle.

In the present invention, the syringe is prepared for reception of vaccine by assembling the needle porton 12 and dust guard 14 to the container portion 10. At this time, however, the lower end of the container portion is open. The syringe is then sterilized by autoclaving or by exposing it to an atmosphere of ethylene oxide at 50 percent relative humidity at a temperature of about 135° F. and at a pressure of between 8–10 psig, for a period of about 5–6 hours. The ethylene oxide gas permeates the polyethylene material of the syringe and the polypropylene material of the dust guard 14 so that the entire syringe becomes sterilized without fear of contamination since there is no later assembly. Following sterilization, the sterilizing chamber is evacuated to remove any traces of ethylene oxide gas from the syringe. It is then filled, asceptically through its open lower end with vaccine diluted to a concentration suitable for human administration. After being filled, the syringe 10 is sealed by heated platens along the line indicated at 22.

The thus filled syringe, along with a plurality of other syringes similarly processed and filled, is placed into a gas and light impervious bag 30 as shown in FIG. 5. The bag 30 and its contents are then sealed and subjected to a very low temperature to freeze the entire package rapidly.

Following this initial freezing operation the bag 30 is placed in an environment maintained at a temperature of from about −10° C to about −20° C, or below, either by a mechanical freezer or by placing the bag 30 in a container of dry ice. As long as the bag 30 is maintained at these freezing temperatures, the vaccine in the syringes does not deteriorate and there is no danger of loss through leakage. Further, because the syringes do not depend upon plunger type actuation, any changes in dimensional relationships between the various syringe components or between the frozen vaccine and the syringe due to freezing, is accommodated without impairment of the final use of the syringes.

The outer bag is to be made of a material which is impervious to light and gas. One such example is the bag 30 shown in FIG. 6 which is basically made of metal foil, such as aluminum foil. This material protects the vaccine in the syringes from both light and undesireable gases, such as carbon dioxide, which might otherwise penetrate the syringe material and reduce the effectiveness of the vaccine.

Figure 6:
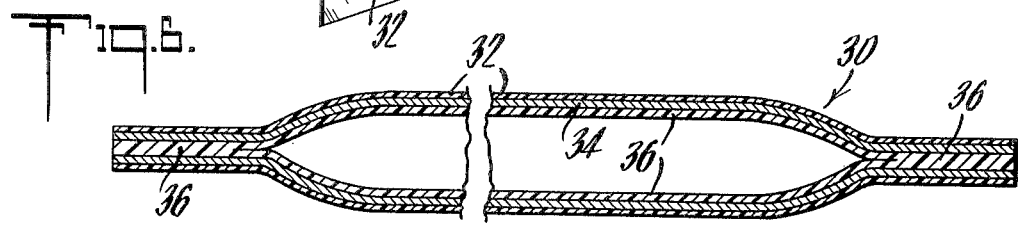
FIG. 6 is an enlarged sectional view taken along line 6—6 of FIG. 5.

In one embodiment of the invention, the bag 30 is of a triple layer material, as can be seen in FIGS. 5 and 6. Thus, the bag 30 has an outer layer 32 of a high density protective plastic material such as polyethylene terephthalate which is sold under the trademark "Mylar." This outer layer, which protects the bag 30 from abrasion and scuffing is preferably about 0.5 mil thick. The outer layer 32 is bonded to a main foil layer 34, preferably of aluminum, having a thickness of about 0.35 mil. The aluminum foil layer 34 serves to prevent entry of light or carbon dioxide gas into the bag. The foil layer 34 is bonded to an inner layer 36 of polyolefin material, such as low density polyethylene, about 3 mil thickness. The inner layer 36 is thermoplastic and serves to seal the edges of the bag 30 together under heat and pressure as shown in FIG. 6.

Figure 7:
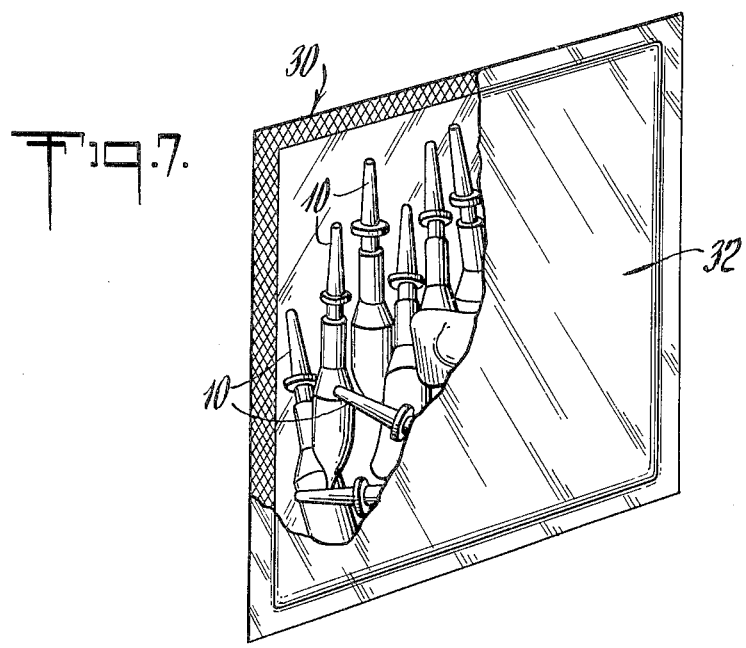
FIG. 7 is a front elevational view, partially cut away, showing a syringe and container assembly according to the present invention.

FIG. 7 shows the bag 30 sealed around frozen vaccine containing the syringes 10.

It will be appreciated that the above described vaccine delivery system provides preloaded single dosage syringe units which are ready for injection with no preparatory manipulation required other than to thaw the syringes and operate and remove the dust guards. The dosage concentration of the vaccine is thus fixed at the site of manufacturing and is not dependent upon vagaries at administration. The system furthermore is not subject to the losses which take place in conventional lyophilization processes. During storage and shipment of the vaccine containing syringes of the present invention, moreover, there is no danger of leakage of vaccine due to its frozen condition.

Although specific embodiments of the invention are herein disclosed for purposes of explanation, various modifications thereof, after study of this specification, will be apparent to those skilled in the art to which the invention pertains.

What is claimed is:

1. A vaccine delivery system suitable for human administration comprising a single dosage hypodermic syringe having a container portion made of a plastic material which is resiliently flexible at room temperature and a needle portion comprising a hollow sharp needle extending from the plastic container portion to convey fluids from within the container out through the tip of the needle when the needle is inserted under the skin and the container is squeezed, an aqueous vaccine diluted to a concentration suitable for human administration and sealed within the container, the vaccine being in the frozen state at a temperature of from about $-10°$ C to about $-20°$ C, whereby the vaccine is preserved for storage and shipment and the syringe is protected from leakage during storage and shipment.

2. A vaccine delivery system according to claim 1 wherein said container portion is composed of low density polyethylene.

3. In combination, a plurality of hypodermic syringes each comprising a tubular container portion of plastic material which is resiliently flexible at room temperature and a needle portion comprising a hollow sharp needle extending out from the container portion, a single dosage of an aqueous vaccine, diluted to a concentration suitable for human administration, contained in each tubular container portion and sealed therein, said vaccine being frozen at a temperature of from about $-10°$ C to about $-20°$ C and a gas and light impervious bag enveloping said plurality of syringes and sealing said syringes therein.

4. A combination according to claim 3 wherein said gas and light impervious bag is of aluminum foil.

5. A combination according to claim 3 wherein said syringes include removable dust covers enveloping the outer end of their needle portion.

6. A method of preparing vaccine for delivery storage and administration comprising the steps of filling tubular flexible syringes having a plastic container portion which is resiliently flexible at room temperature and a hollow sharp needle extending from the plastic container with an aqueous vaccine diluted to human administration concentration, each syringe containing a single dose of the vaccine, sealing the syringes closed, enveloping and sealing a plurality of the filled and sealed syringes inside a gas and light impervious bag, subjecting the filled bag to a temperature low enough to freeze the vaccine and maintaining the vaccine in the bag during storage and shipment at a temperature of from $-10°$ C to about $-20°$ C.

7. A method according to claim 6 further including the step of subjecting the syringe to an ethylene oxide atmosphere prior to filling.

8. A method according to claim 7 further including the step of subjecting the syringe to a vacuum to purge the syringe of ethylene oxide.

9. A method according to claim 6 wherein said filled bag is subjected to a temperature low enough to freeze the vaccine by placing said bag in liquid nitrogen vapors.

10. A method according to claim 6 wherein the bag is maintained at said temperature by placing it in dry ice.

11. A method according to claim 6 wherein the bag is maintained at said temperature by mechanical refrigeration.

* * * * *